(12) United States Patent
Dalmases Barjoan et al.

(10) Patent No.: US 7,563,904 B2
(45) Date of Patent: Jul. 21, 2009

(54) SYNTHESIS INTERMEDIATES USEFUL FOR PREPARING ZOLMITRIPTAN

(75) Inventors: Pere Dalmases Barjoan, Sant Feliu De Llobregat (ES); Montserrat Armengol Asparo, Sant Joan Despi (ES)

(73) Assignee: Inke, S.A., Castellbisbal, Barcelona (ES)

( * ) Notice: Subject to any disclaimer, the term of this patent is extended or adjusted under 35 U.S.C. 154(b) by 75 days.

(21) Appl. No.: 11/940,363

(22) Filed: Nov. 15, 2007

(65) Prior Publication Data

US 2008/0306279 A1 Dec. 11, 2008

Related U.S. Application Data

(62) Division of application No. 10/527,127, filed on Mar. 8, 2005, now Pat. No. 7,342,035.

(51) Int. Cl.
*C07D 263/04* (2006.01)

(52) U.S. Cl. .................. 548/229; 548/215; 548/225

(58) Field of Classification Search .......... 548/215, 548/225, 229
See application file for complete search history.

(56) References Cited

U.S. PATENT DOCUMENTS 7,279,581 B2 * 10/2007 Armengol Asparo et al. ............ 548/266.4

7,342,035 B2 * 3/2008 Armengol Asparo et al. ............... 514/376

FOREIGN PATENT DOCUMENTS

| WO | 91/18897 | 12/1991 |
|---|---|---|
| WO | 97/06162 | 2/1997 |

OTHER PUBLICATIONS

Mooney, et al.; A Novel Series Of 2,5-Substituted Tryptamine Derivatives As Vascular 5HT 1B/1D Receptor Antagonists; J. Med. Chem., 40 (15), 2347-2362, 1997.

* cited by examiner

*Primary Examiner*—Golam M Shameem
(74) *Attorney, Agent, or Firm*—Cozen O'Connor

(57) ABSTRACT

In particular, this invention relates to the synthesis intermediates (IV), (V), (VI) and (VIII) useful for preparing zolmitriptanzohnitriptan or a pharmaceutically acceptable salt thereof, which includes a) Ppreparation of the diazonium salt of the aniline hydrochloride (II); followed by reduction and acidification to give hydrazine (III); b) In situ Reaction of the hydrazine hydrochloride (III) with α-keto-δ-valerolactone, to give the hydrazone (IV); c) Fischer indole synthesis of the hydrazone (IV), to give the pyranoindolone of formula (V); d) Ttransesterification of the pyranoindolone (V) to provide the compound (VI), in which R means a straight or branched C1-C4 alkyl; e) Conversion of the hydroxyl group of the compound (VI) into dimethylamino to give the indolecarboxylate (VII), in which R means a straight or branched C1-C4 alkyl; f) Ssaponification of the 2-carboalkoxy group of the compound (VII), to provide indolecarboxylic acid (VIII); g) Ddecarboxylation of the indolecarboxylic acid (VIII), to provide zolmitriptan and, eventually, to provide a pharmaceutically acceptable salt thereof.

4 Claims, No Drawings

SYNTHESIS INTERMEDIATES USEFUL FOR PREPARING ZOLMITRIPTAN

CROSS-REFERENCE TO RELATED APPLICATION

This application is a divisional of commonly assigned U.S. patent application Ser. No. 10/527,127, filed Mar. 8, 2005, now U.S. Pat. No. 7,342,035 incorporated herein by reference.

FIELD OF THE INVENTION

This invention relates to the synthesis intermediates useful for preparing zolmitriptana new process for preparing a pharmaceutically active compound. In particular, it relates to a process for preparing zolmitriptan.

BACKGROUND OF THE INVENTION

Patent ES 2104708 discloses a class of compounds with special agonism through the 5-HT$_1$-like receptors and excellent absorption following oral administration. These properties make the compounds particularly useful in the treatment of migraine, cluster headache and headache associated with vascular disorders. One of the preferred compounds of that patent is (S)-4-[3-(2-dimethyl-aminoethyl)-1H-indol-5-ylmethyl]-1,3oxazolidin-2-one, known under the INN zolmitriptan, of formula (I):

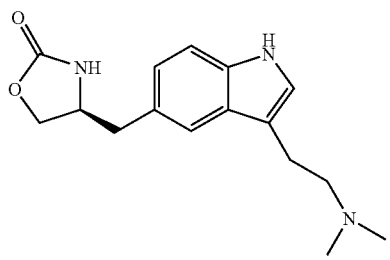

The aforesaid patent describes the preparation of zolmitriptan by Fischer indole synthesis, using the corresponding phenyl hydrazine with an aldehyde. Said process nevertheless requires a stage of column purification of the end product, as well as the use of toxic reagents such as tin chloride for preparing the hydrazine, while it has an overall yield of only 18%.

Later, European patent EP 843672 describes optimised preparation of the intermediate (S)-4-(4-aminobenzyl)-1,3-oxazolidin-2-one in a one pot process (that is, without isolating the intermediates) and preparation of the zolmitriptan on the basis of this intermediate in a second one pot process which includes the formation of the diazonium salt of the intermediate, followed by the Fischer reaction (by addition of 4,4-diethoxy-N,N-dimethylbutilamine). However, this patent does not quote the yield of zolmitriptan obtained. As a result, this applicant has carried out that procedure in order to reproduce and quantify it. The end product was obtained with yields of the order of 30% and with high impurity content due to the one pot reaction. It is therefore a process not applicable at industrial scale, either in terms of yield or of impurities.

DESCRIPTION OF THE INVENTION

A first aspect of the present invention is relates to provide a new process for preparing zolmitriptan or a pharmaceutically acceptable salt thereof, and particularly to the synthesis intermediates useful for preparing it, which comprises the following stages:

a) Preparation of the diazonium salt of the aniline hydrochloride of formula (II)

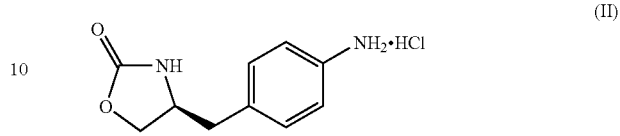

followed by reduction and acidification to give the hydrazine of formula (III):

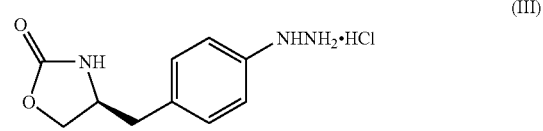

b) In situ reaction of the hydrazine hydrochloride of formula (III) with α-keto-δ-valerolactone to give the hydrazone of formula (IV):

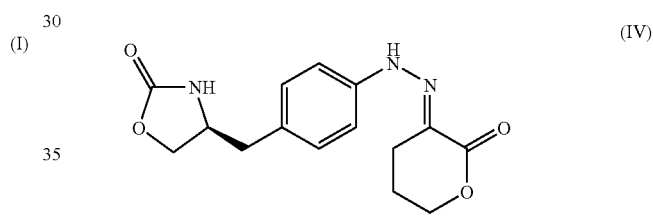

c) Fischer indole synthesis of the hydrazone of formula (IV) to give the pyranoindolone of formula (V):

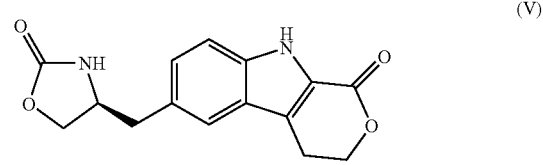

d) Transesterification of the pyranoindolone of formula (V), to provide the compound of formula (VI):

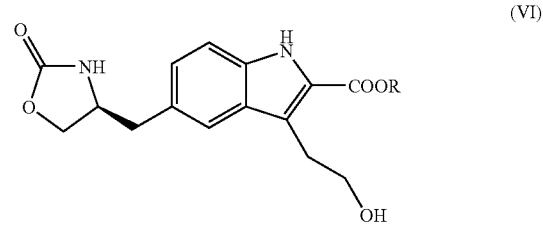

in which R represents a straight or branched C1-C4 alkyl chain;

e) Conversion of the hydroxyl group of the compound of formula (VI) into dimethylamino, to give the indolecarboxylate of formula (VII):

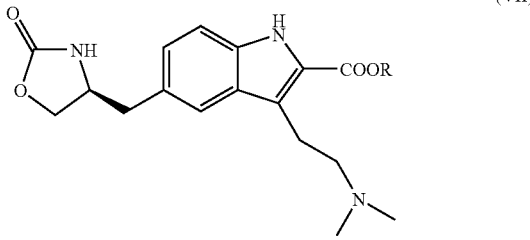

(VII)

in which R represents a straight or branched C1-C4 alkyl chain;

f) Saponification of the 2-carboalkoxy group of the compound of formula (VII), to provide the indolecarboxylic acid of formula (VIII):

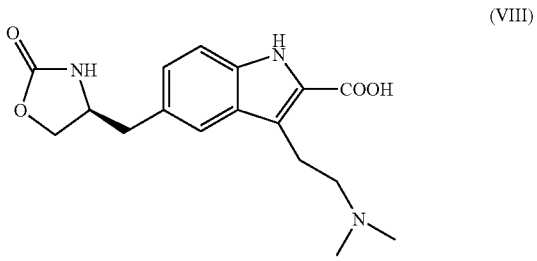

(VIII)

g) Decarboxylation of the indolecarboxylic acid of formula (VIII), to provide zolmitriptan and, eventually, to prepare a pharmaceutically acceptable salt thereof.

Following, each of the steps of the general process for preparing zolmitriptan will be described in more detail.

Preparation of the Diazonium Salt of the aniline hydrochloride of formula (II), in stage a), is carried out by treating this compound with sodium nitrite and hydrochloric acid at low temperature. Subsequent reduction thereof is effected with an alkaline metal sulphite followed by acidification to give the hydrazine of formula (III).

Reaction of the hydrazine hydrochloride of formula (III) with α-keto-δ-valerolactone, in stage b), is carried out in aqueous medium at a temperature between 10° C. and 80° C., preferably at room temperature, and at a pH between 0.1 and 4, preferably at pH 1. The product is isolated by conventional methods.

Stage c), to prepare the compound of formula (V), can be carried out at room temperature in a solution of dry hydrogen in acetic acid, and then the compound isolated by conventional methods.

The transesterification reaction of stage d) can then be carried out in an alcoholic solution, preferably methanol, and in the presence of an acid, preferably methanesulphonic acid. The product is isolated by conventional methods.

Alternatively, stage c) and stage d) can be carried out as a one pot reaction (that is, without isolating intermediates). In this case the Fischer indole synthesis of the hydrazone of formula (IV) followed by transesterification is carried out under conditions similar to those described in patent GB 1189064 for preparing carboalkoxy-indoles. It is thus preferably carried out in a solution of dry hydrogen chloride in a straight or branched C1-C4 alcohol chain (such as methanol, ethanol, etc.). The reaction can be carried out at a temperature between 0° C. and 80° C., preferably between 60° C. and 80° C., to prepare the compound of formula (VI), which is isolated by conventional methods.

Conversion of the hydroxyl group of the compound of formula (VI) into a dimethylamino group, in stage e), is carried out preferably by substituting the hydroxyl group by a leaving group X and subsequent substitution reaction of the leaving group X with dimethylamine. Preferably, X is a halogen atom, a mesylate group (OMs) or a tosylate group, a tosylate group being most preferable.

The replacement of the hydroxyl group of the compound of formula (VI) by a leaving group X can be carried out by reacting it with mesyl chloride or tosyl chloride or by replacing said hydroxyl by a halogen, using conventional halogenating reagents. It is carried out preferably by reaction with tosyl chloride. Thus, when X=OTs, the reaction is carried out in a suitable solvent, such as dichloromethane or toluene, in the presence of pyridine and of 4-(dimethylamino)pyridine as catalyst, and when X=OMs, the reaction is carried out in a suitable solvent, such as tetrahydrofuran, in the presence of triethylamine as catalyst. The reaction can be carried out at a temperature between 0° C. and 50° C., preferably at room temperature. The product is isolated by conventional methods.

In the case of the tosylates, the substitution reaction of the leaving group X with dimethylamine takes place under particularly gentle conditions. This reaction is carried out in an alcoholic solution or in an aqueous solution, at a temperature between 0° C. and 100° C., preferably at 50° C. The product is isolated by conventional methods.

The saponification of the 2-carboalkoxy group of the compound of formula (VII), of stage f), is carried out in alkaline medium, preferably in an alcoholic solution of potassium hydroxide, and at a temperature between 20° C. and 100° C., preferably at reflux temperature. The product is isolated by conventional methods.

The decarboxylation of the indolecarboxylic acid of formula (VIII), of stage g), is carried out in the presence of an inert solvent of high boiling point and a suitable catalyst, in an inert atmosphere and at a temperature between 180° C. and 250° C. Preferably, the solvent is quinoline or a mixture of quinoline and an organic solvent such as triethylene glycol dimethyl ether, diphenyl ether, etc. Catalysts can be chosen from powdered copper, cuprous oxide, cuprous chloride, cupric chromite, copper pentafluorophenyl or the cupric salt of the compound of formula (VIII) used in a molar proportion between 5% and 10% in relation to the compound of formula (VIII). The inert atmosphere can be created by stream of dry nitrogen. The reaction is preferably carried out at 200° C. The product is isolated by conventional methods.

The initial products for carrying out the process described above can be obtained as indicated below.

The aniline hydrochloride of formula (II) can be obtained by reduction of the corresponding nitro derivative, as described in patent ES 2104708, and the α-keto-δ-valerolactone can be obtained by decarboxylation of α-ethoxyalyl-γ-butyrolactone in 2N $H_2SO_4$ at reflux.

The present invention also relates to the synthesis intermediates useful for preparing zolmitriptan.

A first second aspect of the present invention is the synthesis intermediate of formula (IV):

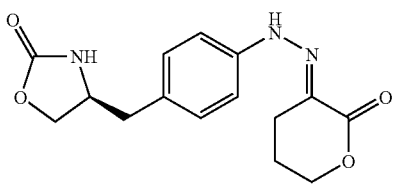

A second third aspect of the present invention is the synthesis intermediate of formula (V):

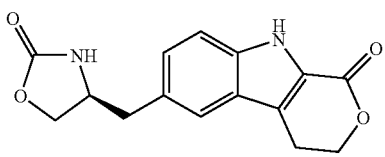

A third fourth aspect of the present invention is a synthesis intermediate of formula (VI):

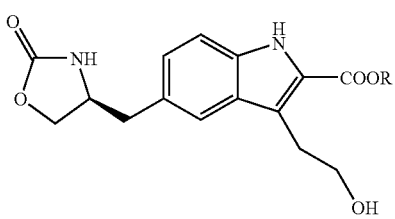

in which R represents a straight or branched C1-C4 alkyl chain.

A fourth fifth aspect of the present invention is the intermediate synthesis intermediate of formula (VIII):

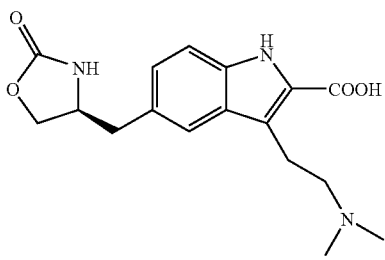

The aforesaid synthesis intermediates of formulae (IV), (V), (VI), (VII) and (VIII) are useful for the synthesis of zolmitriptan, although their use for synthesis of other products likewise forms part of the scope of protection of the present invention.

The stages described above in the general process for providing zolmitriptan can therefore be considered independent processes for preparing the intermediate synthesis products, isolating the intermediate product where necessary.

There follows a description of these stages as independent procedures for preparing each one of the synthesis intermediates.

A first process relates to preparation of the intermediate of formula (IV) by reaction of the hydrazine hydrochloride of formula (III) with α-keto-δ-valerolactone, in accordance with stage b) of the first aspect of the invention.

A second process relates to preparation of the intermediate of formula (V) by Fischer indole synthesis of the hydrazone of formula (IV), in accordance with stage c) of the first aspect of the invention.

A third process relates to preparation of the intermediate of formula (VI), by transesterification of the pyranoindolone of formula (V), in accordance with stage d) of the first aspect of the invention.

A fourth process relates to preparation of the intermediate of formula (VII), by conversion of the hydroxyl group of the compound of formula (VI) into dimethylamino, in accordance with stage e) of the first aspect of the invention.

A fifth process relates to preparation of the intermediate of formula (VIII), by saponification of the 2-carboalkoxy group of the intermediate of formula (VII), in accordance with stage f) of the first aspect of the invention.

For a better understanding of what is outlined some examples are included which, in a non-restrictive manner, show practical cases of embodiment of the invention.

EXAMPLES OF SYNTHESIS

Example 1

(S)-4-{4-[N'-(2-Oxotetrahydropyran-3-iliden) hidrazino]benzyl}-1,3-oxazolidin-2-one A solution of 2.8 g (40.6 nmoles) of sodium nitrite in 12 ml of water was added slowly to a solution of 9.1 g (39.8 mmoles) of (S)-4-(4-aminobenzyl)-1,3-oxazolidyne-2-one hydrochloride in 17 ml of water and 29 ml of concentrated HCl, keeping the reaction temperature below 0° C. The mixture was stirred at this temperature for 15 minutes. Once that time had elapsed the diazonium salt solution was added rapidly to a suspension of 30 g (239 mmoles) of sodium sulphite in 106 ml of water precooled to 0° C. under nitrogen atmosphere. The red solution was stirred at 0° C. for 10 minutes and then left to reach 65° C. in 1 hour. It was stirred at 65° C. for 30 minutes, and 18.2 ml of concentrated HCl then added. The mixture was stirred at the same temperature under nitrogen atmosphere for 3 hours and then left to cool to room temperature. To this solution was added a solution of 63.7 mmoles of α-keto-δ-valerolactone (prepared by decarboxylation of 11.8 g (63.37 mmoles) of α-ethoxyalyl-γ-butyrolactone in 15.2 ml of 2N $H_2SO_4$ at reflux) and left under stirring at room temperature for 12 hours. When that time had elapsed the mixture was cooled to 0° C. and stirred for one hour. The precipitate formed was filtered, washed with cold water and dried in an hot-air oven at 40° C., giving a white solid which was crystallised from ethanol/water to give 10.5 g (87%) of the title hydrazone as a white solid.

M.p. 223.3-224.7° C.

IR (KBr): 1127 $cm^{-1}$, 1250 $cm^{-1}$, 1400 $cm^{-1}$; 1422 $cm^{-1}$, 1544 $cm^{-1}$, 1694 $cm^{-1}$, 1755 $cm^{-1}$.

$^1$H-NMR (200 MHz, DMSO-$d_6$): 1.99 (m, 2H, γ-lactone); 2.59 (m, 4H, β-lactone and $CH_2$-benz.); 3.98 (m, 2H, $OCH_2$); 4.27 (m, 3H, δ-lactone and NHC$\underline{H}$); 7.14 (d, 2H, J=8.4 Hz, ar); 7.24 (d, 2H, J=8.4 Hz, ar); 7.77 (s, 1H, CONH); 10.03 (s, 1H, NH-hydrazone).

¹³C-NMR (200 MHz, DMSO-d₆): 21.3; 24.5; 52.8; 67.5; 68.2; 114.3; 129.5; 130.2; 130.4; 143.0; 158.8; 162.3.

Example 2

(S)-6-(2-Oxo-1,3-oxazolidin-4-ylmethyl)-4,9-dihydro-3H-pyrano-[3,4-b]indol-1-one 3.8 g (12.5 mmoles) of (S)-4-{4-[N'-(2-oxotetrahydropyran-3-iliden) hydrazine]benzyl}-1,3-oxazolidin-2-one were suspended in 32 ml of a saturated solution of hydrogen chloride in acetic acid. The mixture was stirred at room temperature for 16 h, 10 ml of water/ice was added to the reaction mixture and stirred at 0° C. for 20 min. The precipitate was filtered, washed with cold water and dried in hot-air oven at 40° C. The residue was crystallised with methanol to yield 3.3 g (92%) of the title indole as a yellow crystalline solid.

M.p. 215-217° C.

IR (KBr): 1400, 1705, 1733, 3355 cm⁻¹.

¹H-NMR (200 MHz, DMSO-d₆): 2.85 (t, J=4.8 Hz, 2H, C$\underline{H}_2$-benz.); 3.09 (t, J=6.4 Hz, 2H, δ-lactone); 4.04 (m, 2H, OC$\underline{H}_2$); 4.26 (m, 1H, NHC$\underline{H}$); 4.62 (t, J=6.4 Hz, 2H, γ-lactone); 7.21 (d, J=8.6 Hz, 1H, ar); 7.36 (d, J=8.6 Hz, 1H, ar); 7.55 (s, ar), 7.81 (s,1H, CONH); 11.88 (s, 1H, NH-indole).

¹³C-NMR (200 MHz, DMSO): 21.0; 53.0; 68.2; 69.2; 112.9; 121.3; 122.2; 122.6; 124.4; 127.9; 128.3; 137.3; 158.8; 160.5.

Example 3

(S)-3-(2-Hydroxyethyl)-5-(2-oxo-1,3-oxazolidin-4-ylmethyl)-1H-indol-2-carboxylic acid methyl ester To a suspension of 500 mg (1.74 mmoles) of the (S)-6-(2-oxo-1,3-oxazolidin-4-ylmethyl)-4,9-dihydro-3H-pyrano-[3,4-b]indol-1-one in 10 ml of methanol were added 0.12 ml (1.9 mmoles) of methanesulphonic acid. The mixture was left under stirring at the reflux temperature for 3 hours. The solvent was evaporated to dryness under reduced pressure, the residue dissolved with 10 ml of a saturated bicarbonate solution and extracted three times with dichloromethane. The combined organic phases were dried and evaporated to dryness and the evaporated solid recrystallised from ethanol to give 517 mg (93%) of the title ester as a yellow crystalline solid.

M.p. 178-180° C.

IR (KBr): 1427, 1555, 1695, 1738, 3354 cm⁻¹.

¹H-NMR (200 MHz, DMSO-d₆): 2.85 (m, 2H, CH₂-benz.); 3.21 (m, 2H, C$\underline{H}_2$CH₂OH); 3.60 (m, 2H, CH₂C$\underline{H}_2$OH); 3.87 (s, 3H, CH₃); 4.03 (m, 2H, OCH₂); 4.26 (m, 1H, NHC$\underline{H}$); 4.67 (t, J=5.2 Hz, 1H, OH); 7.13 (d, J=8.4 Hz, 1H, ar); 7.33 (d, J=8.4 Hz, 1H, ar); 7.54 (s, 1H, ar); 7.82 (s, 1H, CONH); 11.47 (s, 1H, NH-indole).

Example 4

(S)-3-(2-Hydroxyethyl)-5-(2-oxo-1,3-oxazolidin-4-ylmethyl)-1H-indol-2-carboxylic acid ethyl ester 9.5 g (31.3 mmoles) of S)-4-{4-[N'-(2-oxotetrahydropyran-3-ilyden) hydrazine]benzyl}-1,3-oxazolidin-2-one were suspended in 76 ml of a 2N solution of hydrogen chloride in absolute ethanol. The mixture was left under stirring at 75° C. for 30 min. The solvent was evaporated to dryness under reduced pressure, 50 ml of a saturated solution of potassium carbonate added, and then extracted three times with 50 ml of dichloromethane. The combined organic phases were dried on anhydrous sodium sulphate and evaporated to dryness. The residue was recrystallised from isopropyl alcohol/heptane to give 9.25 g (89%) of the title indole. The product was recrystallised from methanol to give a yellow crystalline solid.

M.p. 154-156° C.

IR (KBr): 1244 cm⁻¹, 1688 cm⁻¹, 1744 cm⁻¹, 3300 cm⁻¹.

¹H-NMR (200 MHz, DMSO-d₆): 1.34 (t, J=7.0 Hz, 3H, OCH₂C$\underline{H}_3$); 2.84 (m, 2H, CH₂–benz.); 3.20 (m, 2H, C$\underline{H}_2$CH₂OH); 3.58 (m, 2H, CH₂C$\underline{H}_2$OH); 4.02 (m, 2H, OCH₂); 4.31 (m, 3H, OC$\underline{H}_2$CH₃ and NHC$\underline{H}$); 4.65 (t, J=5.4 Hz, 1H, OH); 7.12 (dd, J=0.8 and 8.4 Hz. 1H, ar); 7.33 (d, J=8.4 Hz, 1H, ar); 7.52 (s, 1H, ar); 7.81 (s, 1H, CONH); 11.41 (s, 1H, NH-indole).

¹³C-NMR (200 MHz, DMSO-d₆): 15.0; 29.2; 41.2; 53.7; 60.8; 62.4; 68.8; 113.1; 120.6; 121.5; 124.3; 127.4; 128.1; 128.5; 136.0; 159.4; 162.4.

Example 5

(S)-5-(2-Oxo-1,3-oxazolidin-4-ylmethyl)-3-[(2-toluen-4-sulphonyloxy) ethyl]-1H-indol-2-carboxylic acid ethyl ester To a stirred suspension of 4.6 g (13.8 mmoles) of the (S)-3-(2-hydroxyethyl)-5-(2-oxo-1,3-oxazolidin-4-ylmethyl)-1H-indol-2-carboxylic acid ethyl ester in 42 ml of dichloromethane were added 4.2 ml of pyridine, 3.9 g (20.7 mmoles) of tosyl chloride and 170 mg (1.38 mmoles) of dimethylaminopyridine and the stirring continued at room temperature for 20 hours. The reaction mixture was poured over 20 ml of 3N HCl precooled to 0° C. and extracted twice with 40 ml of dichloromethane. The combined organic phases were washed with brine, dried on anhydrous sodium sulphate and the solvent evaporated to dryness. The evaporated solid was crystallised with isopropyl alcohol to give 6.4 g (95%) of the title compound as a white crystalline solid.

M.p. 166.4-168.2° C.

IR(KBr): 1154 cm⁻¹, 1238 cm⁻¹, 1312 cm⁻¹, 1705 cm⁻¹, 1722 cm⁻¹, 1766 cm⁻¹.

¹H-NMR (200 MHz, DMSO-d₆): 1.28 (t, J=72 Hz, 3H, OCH₂C$\underline{H}_3$); 2.37 (s, 3H, CH₃); 2.82 (m, 2H, C$\underline{H}_2$CH₂OTs); 332 (t, J=6.4 Hz, 2H, CH₂-benz.); 400 (m, 3H, CH₂C$\underline{H}_2$OTs and NCH$\underline{H}$); 4.25 (4H, m, OC$\underline{H}_2$CH₃ and OCH₂); 7.13 (d, J=8.4 Hz, 1H, ar); 7.38 (m, 6H, ar); 7.82 (s, 1H, CONH); 11.56 (s, 1H, NH-indole).

¹³C-NMR (200 MHz, DMSO-d₆): 14.3; 21.2; 24.3; 40.6; 53.11; 60.4; 68.2; 70.4; 112.6; 116.5; 120.4; 126.9; 127.3; 127.6; 127.8; 129.9; 132.2; 135.2; 144.7; 158.8; 161.4.

Example 6

(S)-3-(2-Dimethylaminoethyl)-5-[2-oxo-1,3-oxazolidin-4-ylmethyl]-1H-indol-2-carboxylic acid ethyl ester A stirred suspension of 5 g (10.3 mmoles) of (S)-5-(2-oxo-1,3-oxazolidin-4-ylmethyl)-3-[(2-toluen-4-sulphonyloxy) ethyl]-1H-indol-2-carboxylic acid ethyl ester in 30 ml of a 2N solution of dimethylamine in ethanol was stirred at 50° C. for 20 hours in a closed reactor. The solvent was evaporated to dryness, the residue dissolved in 20 ml of 2N HCl and washed three times with 15 ml of dichloromethane. The washed aqueous phase was cooled and adjusted to pH 12 with a 40% sodium hydroxide solution and extracted three times with 20 ml of dichloromethane. The combined organic phases were washed with brine and dried on anhydrous sodium sulphate. The solvent was evaporated to dryness and the residue recrystallised from ethyl acetate to give 3.4 g (91%) of the title dimethylamine as a yellow solid.

M.p. 67-70° C.

IR (KBr): 1333 cm$^{-1}$, 1711 cm$^{-1}$, 1745 cm$^{-1}$.

$^1$H-NMR (200 MHz, DMSO-d$_6$): 1.35 (t, J=7.0 Hz, 3H, OCH$_2$CH$_3$); 2.23 (S, 6H, N(CH$_3$)$_2$); 2.45 (m, 2H, CH$_2$CH$_2$N); 2.86 (m, 2H, CH$_2$CH$_2$N); 3.18 (m, 2H, CH$_2$-benz.); 4.05 (m, 2H, OCH$_2$); 4.34 (m, 3H, OCH$_2$CH$_3$ and NHCH); 7.14 (dd, J=1.2 and 8.4 Hz, 1H, ar); 7.35 (d, J=8.4 Hz, 1H, ar); 7.52 (s, 1H, ar); 7.82 (s, 1H, CONH); 11.47 (s, 1H, NH-indole).

$^{13}$C-NMR (200 MHz, DMSO-d$_6$): 14.5; 22.5; 40.9; 45.2; 53.1; 60.2; 60.3; 68.1; 112.5; 120.7; 121.1; 123.5; 126.9; 127.5; 127.6; 135.5; 158.8; 161.9.

Example 7

(S)-3-(2-Dimethylaminoethyl)-5-(2-oxo-1,3-oxazolidin-4-ylmethyl)-1H-indol-2-carboxylic acid To a solution of 1.4 g (24.9 mmoles) of KOH in 30 ml of ethanol was added 2.8 g (7.8 mmoles) of (S)-3-(2-dimethylaminoethyl)-5-[2-oxo-1,3-oxazolidin-4-ylmethyl]-1H-indol-2-carboxylic acid ethyl ester. The resulting solution was heated at reflux temperature for one hour. It was cooled and the solvent evaporated to dryness. The residue was dissolved in 6 ml of water and washed three times with 10 ml of dichloromethane. The aqueous solution was cooled to 5° C., adjusted to pH 6 with glacial acetic acid, stirred for 30 minutes at that temperature and the water evaporated to dryness. The residue was redissolved in 30 ml of water and 5 g of ionic exchange resin (Dowex 50WX8-400) added. The mixture was left under stirring at room temperature for 24 hours. The resin was filtered and it was washed with water. For desorption the resin was suspended with 20 ml of a 10% aqueous solution of ammonia and stirred at room temperature for 5 hours. Once that time had elapsed it was filtered and washed with water. The water was evaporated to dryness under reduced pressure to give 7.75 g (94%) of the title acid as a yellow crystalline solid:

M.p. 230° C.

IR (KBr): 1342 cm$^{-1}$, 1403 cm$^{-1}$, 1587 cm$^{-1}$, 1739 cm$^{-1}$, 3430 cm$^{-1}$.

$^1$H-NMR (200 MHz, DMSO-d$_6$): 2.47 (s, 6H. N(CH$_3$)$_2$), 2.87 (m, 4H, CH$_2$CH$_2$N), 3.27 (m, 2H, CH$_2$-benz.); 4.03 (m, 2H, OCH$_2$); 4.27 (m, 1H, NHCH), 6.98 (d, J=8,0 Hz, 1H, ar), 7.27 (d, J=8.0 Hz, 1H, ar), 7.41 (s, 1H, ar); 7.83 (s, 1H, CONH), 10.95 (s, 1H, NH-indole).

$^{13}$C-NMR (200 MHz, DMSO-d$_6$): 21.15; 43.7; 53.3; 59.7; 68.2; 112.1; 113.2; 119.7; 124.4; 126.4; 128.1; 132.2; 134.0; 158.9; 166.2.

Example 8

(S)-4-[3-(2-Dimethylaminoethyl)-1H-indol-5-ylmethyl]-1,3-oxazolidin-2-one 1 g (3.02 mmoles) of the (S)-3-(2-dimethylaminoethyl)-5-(2-oxo-1,3-oxazolidin-4-ylmenthyl)-1H-indol-2-carboxylic acid was suspended in 10 ml of dry quinoline. 20 mg of cuprous oxide was added and the stirred suspension heated to 200° C. under dry nitrogen stream. The reaction mixture was kept at this temperature until no more CO$_2$ was released (15-20 min.). It was left to cool to room temperature and the reaction mixture filtered through decalite. The filtrate was concentrated by vacuum distillation of the solvent, providing a residue which was dissolved with a succinic acid solution and washed three times with 15 ml of dichloromethane. The washed aqueous phase was cooled, the pH adjusted to 12 with a 40% sodium hydroxide solution and extracted three times with 20 ml of dichloromethane. The combined organic phases were dried on anhydrous sodium sulphate and evaporated to dryness. The residue was recrystallised with isopropyl alcohol to give 780 mg (90%) of zolmitriptan as a white solid.

M.p. 138-140° C.

IR (KBr): 1237 cm$^{-1}$, 1443 cm$^{-1}$, 1743 cm$^{-1}$.

$^1$H-NMR (200 MHz, CDCl$_3$): 2.34 (s, 6H, N(CH$_3$)$_2$), 2.67 (m, 2H, CH$_2$CH$_2$N), 2.93 (t, 4H, CH$_2$CHN and CH$_2$-benz.), 4.14 (m, 2H, OCH$_2$), 4.43 (m, 1H, NHCH); 5.60 (ba, 1H, NH-indole); 6.94 (dd, J=1.2 and 8.6 Hz, 1H, ar); 7.01 (d, J=1.2 Hz, 1H, ar); 7.28 (d, J=8.6 Hz, 1H, ar), 7.37 (s, 1H, ar), 8.49 (s, 1H, CONH).

$^{13}$C-NMR (200 MHz, CDCl$_3$): 23.5; 41.6; 45.3; 54.3; 60.1; 67.7; 111.6; 113.8; 118.8; 122.4; 122.7; 126.4; 127.8; 135.4; 159.3.

We claim:

1. A compound of formula (IV):

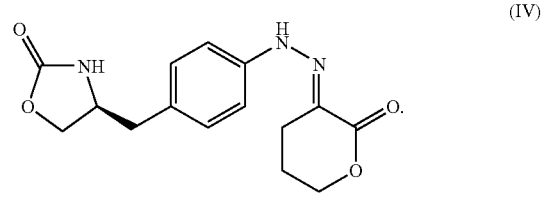

(IV)

2. A compound of formula (V):

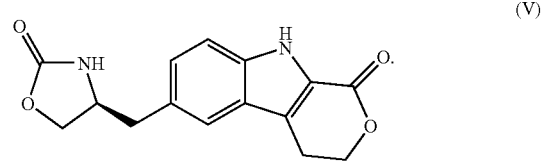

(V)

3. A compound of formula (VI):
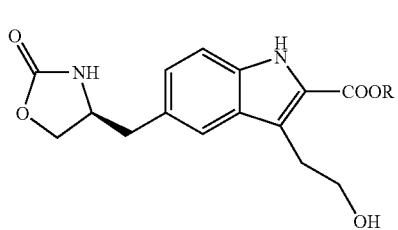
where R represents a straight or branched C1-C4 alkyl chain.
4. A compound of formula (VIII):
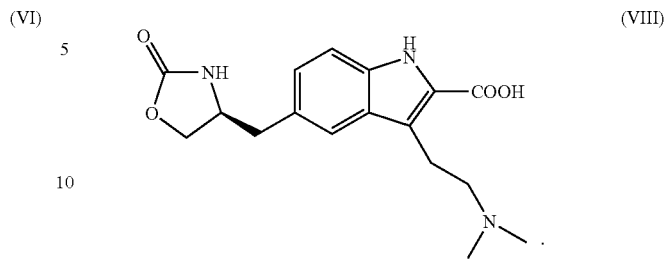
* * * * *